United States Patent
Kim et al.

(10) Patent No.: US 9,756,317 B2
(45) Date of Patent: Sep. 5, 2017

(54) HOLOGRAPHIC DISPLAY METHOD AND APPARATUS USING OPTICAL FIBER ARRAY BACKLIGHT FOR PORTABLE DEVICE

(71) Applicant: ELECTRONICS AND TELECOMMUNICATIONS RESEARCH INSTITUTE, Daejeon (KR)

(72) Inventors: Hyun Eui Kim, Cheongju-si (KR); Jin Woong Kim, Daejeon (KR); Kyung Ae Moon, Daejeon (KR); Min Sik Park, Sejong (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 204 days.

(21) Appl. No.: 14/600,806

(22) Filed: Jan. 20, 2015

(65) Prior Publication Data
US 2015/0205259 A1   Jul. 23, 2015

(30) Foreign Application Priority Data
Jan. 20, 2014   (KR) .................. 10-2014-0006872

(51) Int. Cl.
*H04N 13/04* (2006.01)
*A61B 3/113* (2006.01)
(Continued)

(52) U.S. Cl.
CPC ......... *H04N 13/0409* (2013.01); *A61B 3/113* (2013.01); *G02B 6/0006* (2013.01);
(Continued)

(58) Field of Classification Search
CPC ........ G03H 1/02; G03H 1/2294; G03H 1/265; G03H 2222/18; G03H 2222/13;
(Continued)

(56) References Cited

U.S. PATENT DOCUMENTS

| 6,018,402 A | 1/2000 | Campbell et al. |
| 2006/0050374 A1* | 3/2006 | Slinger ................ G03H 1/2205 359/385 |
| 2008/0088935 A1* | 4/2008 | Daly .................. H04N 13/0454 359/613 |
| 2009/0147331 A1* | 6/2009 | Ashkenazi ............... G02B 5/32 359/13 |
| 2009/0189974 A1* | 7/2009 | Deering .................. G09G 3/02 348/46 |

(Continued)

FOREIGN PATENT DOCUMENTS

KR   10-2013-0094108 A   8/2013

OTHER PUBLICATIONS

Lee et al. (Face and eye tracking for sub-hologram based digital holographic display system, Proc. of SPIE vol. 8384, pp. 838403-1-838403-9 [2012]).*

*Primary Examiner* — Kimberly N Kakalec
(74) *Attorney, Agent, or Firm* — NSIP Law

(57) ABSTRACT

The present invention discloses a holographic display apparatus including a light irradiating unit configured to irradiate light using an optical fiber array backlight, a spatial light modulator (SLM) configured to perform modulating the irradiated light, a lens configured to irradiate hologram images based on the modulated light, a pupil tracking unit configured to acquire location of an observer's pupil by pupil tracking, and a hologram generating unit configured to generate parallax hologram images that correspond to the location of pupil.

15 Claims, 7 Drawing Sheets

(51) Int. Cl.
*G03H 1/22* (2006.01)
*G02B 6/27* (2006.01)
*G02B 27/00* (2006.01)
*F21V 8/00* (2006.01)

(52) U.S. Cl.
CPC ....... *G02B 6/2706* (2013.01); *G02B 27/0025* (2013.01); *G02B 27/0093* (2013.01); *G03H 1/2286* (2013.01); *G03H 1/2294* (2013.01); *G03H 2001/221* (2013.01); *G03H 2001/2236* (2013.01); *G03H 2223/16* (2013.01); *G03H 2226/05* (2013.01)

(58) Field of Classification Search
CPC ........... G03H 2225/12; G03H 2226/05; G02H 2001/0208; G02H 2001/0212; G02H 2001/0216; G02H 2001/0224
See application file for complete search history.

(56) References Cited

U.S. PATENT DOCUMENTS

| | | | |
|---|---|---|---|
| 2010/0188719 A1 | 7/2010 | Leister | |
| 2012/0050830 A1* | 3/2012 | Yoon | G03H 1/22 359/11 |
| 2012/0099170 A1* | 4/2012 | Shikii | G02B 27/01 359/3 |
| 2012/0105929 A1* | 5/2012 | Sung | G03H 1/2286 359/9 |

* cited by examiner

HOLOGRAPHIC DISPLAY METHOD AND APPARATUS USING OPTICAL FIBER ARRAY BACKLIGHT FOR PORTABLE DEVICE

CROSS-REFERENCE TO RELATED APPLICATIONS

This application claims the benefit of priority of Korean Patent Application No. 10-2014-0006872 filed on Jan. 20, 2014, all of which are incorporated by reference in their entirety herein.

BACKGROUND OF THE INVENTION

Field of the Invention

The present invention relates to a method and apparatus for holographic display, and more particularly, to a digital holographic display method and apparatus having a small and compact structure suitable for portable electronic device.

Discussion of the Related Art

The digital holographic display is a display that reproduces phase of light waves, and expresses 3-dimensional images by modulating incident coherent light waves in order to express the phase information of light waves for an object. Since the 3-dimensional images played in a space using the holographic display provides a monocular depth recognition factor such as an accommodation effect, it is available for the holographic display to solve the accommodation-convergence mismatch that the conventional 3-dimensional display based on stereoscopy has.

The size and viewing angle of the hologram image played correlates with data capacity of spatial light modulator (SLM) which is used for modulating amplitude and phase of the incident light waves, which is spatial bandwidth representing the amount of information that optical signals have. Accordingly, the technology for expanding spatial bandwidth has been sustainably developed for increasing the size and viewing angle of a screen which is played on the digital holography.

The digital holographic display technology is considered as an ideal 3-dimensional display technology, but still has many technical problems for commercialization. One of the serious problems is extremely small size and viewing angle of the screen of the hologram played due to the narrow spatial bandwidth of the spatial light modulator. As the spatial bandwidth is proportional to the number of pixel of the spatial light modulator, the spatial bandwidth can be expanded by using multiple spatial light modulators, which is called a holographic stereogram technology. However, the holographic stereogram technology has problems such as very bulky volume due to a plurality of equipments installed for the spatial light modulator, complicated optical structures, and high cost of equipment accordingly, and so the head mounted display or the near eye display which is a display that makes the best use of the narrow spatial bandwidth is the most potential holographic display to be commercialized. However, these eyeglass-type displays have a limited utilization since there are restrictions in watching 3-dimensional images smoothly due to the shortcoming that users wear the display personally to watch the 3-dimensional images, consequently, it is required to develop a portable holographic display of glassless mode that makes the best use of the narrow spatial bandwidth.

SUMMARY OF THE INVENTION

An object of the present invention to solve the problem of described above is to provide a digital holographic display method and apparatus which can implement the holographic display with a low cost and miniaturized structure.

According to an aspect of the present invention, a holographic display apparatus may include a light irradiating unit configured to irradiate light using an optical fiber array backlight, a spatial light modulator (SLM) configured to perform modulating the irradiated light, a lens configured to irradiate hologram images based on the modulated light, a pupil tracking unit configured to acquire location of an observer's pupil by pupil tracking, and a hologram generating unit configured to generate parallax hologram images that correspond to the location of pupil.

The hologram generating unit may change a location of viewing window by performing off-axis hologram encoding when generating hologram in order to supplement a spatial gap between viewing windows.

The light irradiating unit may include an optical fiber laser and an optical fiber.

The light irradiating unit may include an optical fiber coupler configured to diverge the optical fiber laser beam into a plurality of paths and a RGB combiner configured to generate white light using the diverged optical fiber laser beam.

The light irradiating unit may include a half wave polarizing plate and polarizing plate installed between respective optical fibers that are diverged into several parts in order to control a polarization direction of incident beam and power of light, and a light collimator installed at a terminal of the optical fiber in order to irradiate plane waves to the spatial light modulator.

The light irradiating unit may include a viewing window array by arranging the light source array in an arc shape with respect to horizontal and vertical directions.

The holographic display apparatus may further include a noise mask configured to filter diffracted high-order terms and twin images.

The lens may be a field flattener lens, and the viewing window may be formed at a focal distance by focusing the modulated light into a focal point of the lens.

The pupil tracking unit may include a stereo camera and an infrared LED.

According to another aspect of the present invention, a holographic display method may include irradiating light using an optical fiber array backlight, modulating the irradiated light performed by a spatial light modulator (SLM), irradiating hologram images by passing the modulated light through a lens, tracking pupil for acquiring location of an observer's pupil by pupil tracking, and generating parallax hologram images that correspond to the location of pupil.

The step of generating the hologram images may include changing a location of viewing window by performing off-axis hologram encoding when generating hologram in order to supplement spatial gap between viewing windows.

The step of irradiating the light may include generating white light using an optical fiber laser and an optical fiber.

The step of irradiating the light may include diverging the optical fiber laser beam into a plurality of paths, and generating white light through a RGB combiner.

The step of irradiating the light may include controlling a polarization direction of incident beam and power of light by installing a half wave polarizing plate and polarizing plate between respective optical fibers that are diverged into several parts, and irradiating a plane wave to the spatial light modulator through a light collimator installed at a terminal of the optical fiber.

The step of irradiating the light may include forming a viewing window array by arranging a light source array in an arc shape with respect to horizontal and vertical directions.

The holographic display method may further including filtering diffracted high-order terms and twin images by a noise mask.

The lens may be a field flattener lens, and irradiating the hologram may include forming a viewing window at a focal distance by focusing the modulated light into a focal point of the lens.

The step of tracking the pupil may include acquiring the location of the observer's pupil using a stereo camera and an infrared LED.

BRIEF DESCRIPTION OF THE DRAWINGS

The accompanying drawings, which are included to provide a further understanding of the present invention and constitute a part of specifications of the present invention, illustrate embodiments of the present invention and together with the corresponding descriptions serve to explain the principles of the present invention.

DETAILED DESCRIPTION OF THE INVENTION

Figure 1:
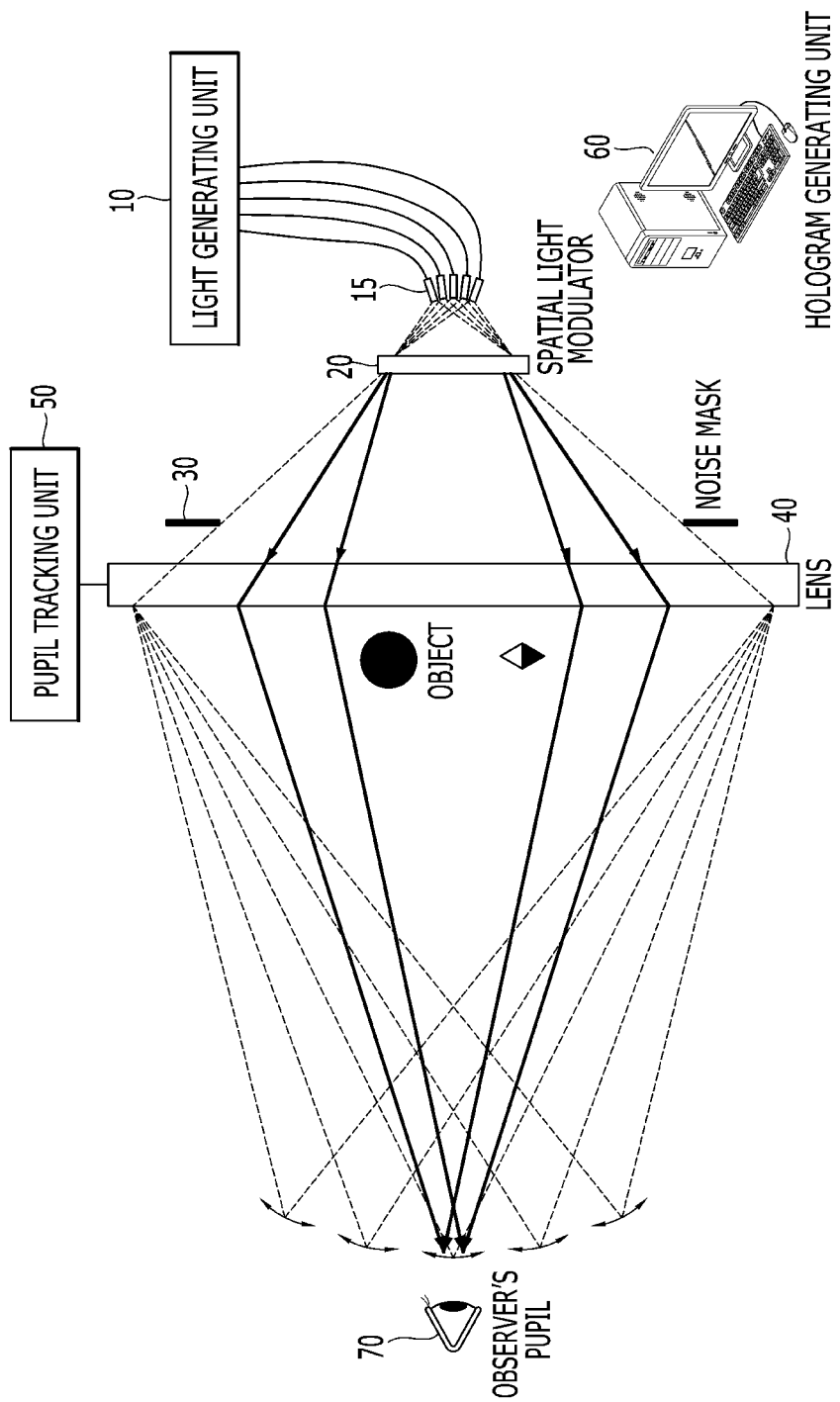
FIG. 1 is a block diagram schematically illustrating the construction of the holographic display apparatus according to an embodiment of the present invention.

The inventive subject matter now will be described more fully hereinafter with reference to the accompanying drawings, in which embodiments of the present invention are shown.

However, the present invention may be embodied in many different forms, modifications, equivalents and alternatives, which are included in the inventive concept and scope, and should not be construed as limited to the embodiments set forth herein.

Although the terms first, second, etc. may be used herein to describe various elements, it will be understood that these elements should not be limited by these terms. These terms are only used to distinguish one element from another. For example, a first element could be termed a second element, and similarly, a second element could be termed a first element without departing from the scope of the present invention. Herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening element present.

The terminology used herein is for the purpose of describing particular embodiments only and is not intended to be limiting of the present invention. As used herein, the singular forms are intended to include the plural forms as well, unless the context clearly indicates otherwise. It will be further understood that the terms "comprise" or "include" etc. when being used in this specification specify the presence of stated features, numbers, steps, operations, elements, components or combination of these things, but do not preclude the presence or addition of one or more other features, numbers, steps, operations, elements, components or combination of these things.

Unless otherwise defined, all terms including technical or scientific terms used herein have the same meaning as commonly understood by one of ordinary skill in the art to which the present invention belongs. It will be further understood that the terms such as those defined in commonly used dictionary should be interpreted as having a meaning that is consistent with their meaning in the context of the relevant art, and will not be interpreted in an idealized or overly formal sense unless expressly so defined herein.

The inventive subject matter now will be described more fully hereinafter by reference to the accompanying drawings, in which embodiments of the present invention are shown. In describing embodiments of the present invention, the same reference numeral is used for the same element even in order to be easily understood throughout the specification, and the redundant description for the same element will be omitted.

The digital holographic display apparatus according to an embodiment of the present invention may display the hologram having a wide viewing angle by using a spatial light modulator, elements in relation to pupil tracking and optical fiber array backlight. According to an embodiment of the present invention, in order to be applied to a miniaturized apparatus, the digital holographic display apparatus may be constructed with one spatial light modulator, which is made up for the drawback that has a restricted spatial bandwidth to make the best use of the spatial bandwidth so as to expand the scale of images played through hologram projection lens played by the spatial light modulator. In this time, since the digital holographic display apparatus has the structure that maximize screen size by minimizing viewing angle in the relation of the screen size and the viewing angle which is trade-off relation, the system does not require relatively high spatial bandwidth. Accordingly, it is available to play large scaled hologram even by the spatial light modulator whose pixel gap and pixel number are not big. However, in this structure, since the viewing angle of the hologram images played becomes extremely narrow, in order to supplement this, the system may be constructed to have the elements in relation to the backlight using the pupil tracking and optical fiber array.

FIG. 1 is a block diagram schematically illustrating the construction of the holographic display apparatus according to an embodiment of the present invention. As shown in FIG. 1, the holographic display apparatus according to an embodiment of the present invention may include a light irradiating unit including a generating unit 10 and a light collimator 15, a spatial light modulating unit 20, a noise mask 30, a lens 40, a pupil tracking unit 50 and a hologram generating unit 60.

Referring to FIG. 1, the light irradiating unit may include the generating unit 10 and the light collimator 15. The light generating unit 10 generates light source through a laser, and the like. In irradiating the light generated by the spatial light modulating unit 20, the light collimator 15 is to irradiate the collimated coherent light having the same area as that of the spatial light modulating unit 20. The light generating unit 10 and the light collimator 15 may be connected through an optical fiber. A plurality of the light collimators 15 and optical fibers may construct an optical fiber array. Detailed description for the light irradiating unit will be described through referring to FIG. 2 below.

The spatial light modulating unit 20 may modulate the light irradiated through the light irradiating unit. The spatial light modulating unit 20 may play hologram images by performing the amplitude and phase modulation of the irradiated light. The hologram images played with being modulated by the spatial light modulating unit 20 may be enlarged the played images through a projection lens having large diameter. According to an embodiment of the present invention, it may be applied that the hologram image magnifying play method in which the light entering to viewing window of an observer focuses. As described above, since the viewing angle of the hologram images played by the structure becomes extremely narrow, it is required for the construction related to the backlight using the tracking of an observer's pupil 70 and optical fiber array in order to supplement the narrow viewing angle. In particular, the spatial light modulating unit 20 may include one spatial light modulator, since it is equipped with the construction related to the backlight using the tracking of an observer's pupil 70 and the optical fiber array. Also, it may be permissible to use the spatial light modulator whose pixel gap and the pixel number are smaller than reference values.

The noise mask 30 may play the role of eliminating twin images and high-order terms of the hologram played by limiting the viewing window region.

The lens 40 may play the role of irradiating hologram images based on the light which is modulated by the spatial light modulating unit 20. According to an embodiment of the present invention, the lens 40 may be a field flattener lens having large diameter. The light modulated by the spatial light modulator 20 is concentrated on the focal point of the lens 40, and forms a viewing window at the focal distance. In this time, the object generated by the hologram played may be generated on the region where the respective regions of diamond shape, which are formed based on the light emitted from each of the light collimators 15.

The pupil tracking unit 50 may acquire the location of the pupil 70 of an observer in order to produce the hologram images which is suitable for parallax. The acquired location of the pupil 70 may be used for inferring an observer's view point or focusing light waves on the view point of the observer. The pupil tracking unit 50 may be disposed in front of the hologram display. The pupil tracking unit 50 may include a stereo camera, may acquire the location of the pupil 70 of the observer through this, and display the hologram images with the parallax that corresponds to the location.

The hologram generating unit 60 may generate hologram images having a parallax that corresponds to the location of the observer's pupil 70 which is obtained by the pupil tracking unit 50. The beams incident into the spatial light modulating unit 20 is modulated and diffracted through the computer generated hologram (CGH) which is generated by the hologram generating unit 60. In addition, the hologram generating unit 60 may generate the hologram images to be located to the location of the observer's pupil through the rotation of the axis of input images according to the optical axis of respective viewing windows which are generated by the light array of the light irradiating unit. And, according to an embodiment of the present invention, in order to supplement the spatial gap between the viewing windows which are arrayed by respective light sources, the hologram generating unit 60 may perform off-axis hologram encoding when generating hologram, thereby change the locations of the viewing windows.

Figure 2:
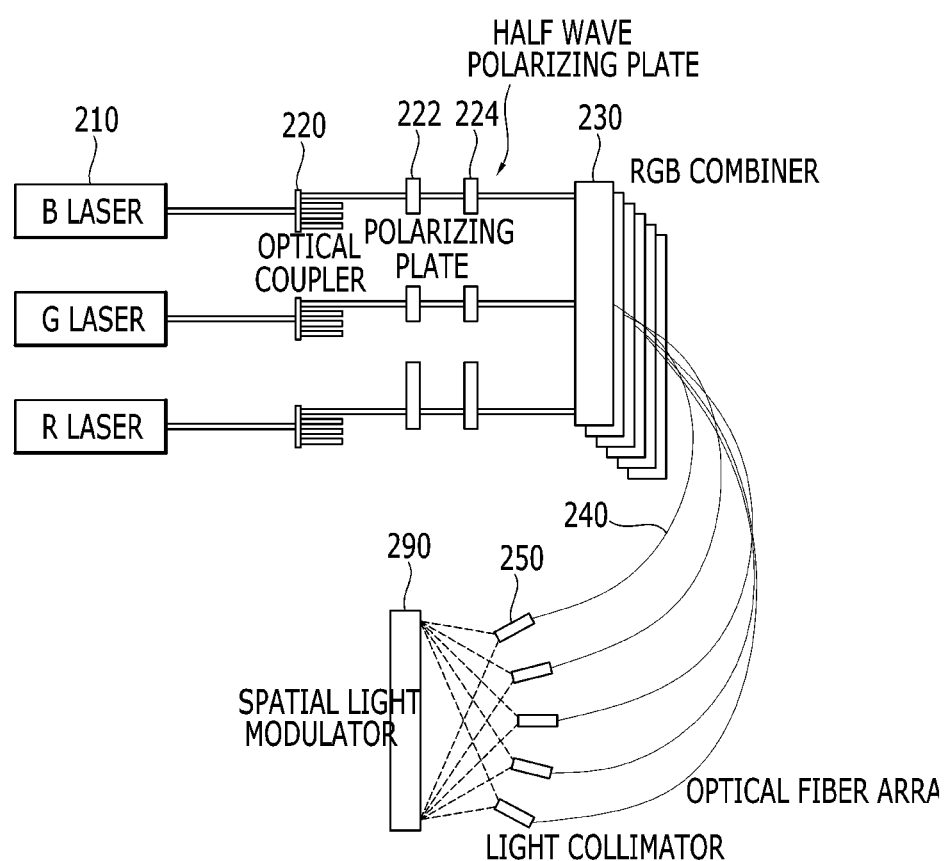
FIG. 2 is a detailed block diagram illustrating the construction of the light irradiating unit of the holographic display apparatus in detail according to an embodiment of the present invention.

FIG. 2 is a detailed block diagram illustrating the construction of the light irradiating unit of the holographic display apparatus in detail according to an embodiment of the present invention. As depicted in FIG. 2, the light irradiating unit 200 according to an embodiment of the present invention may include a laser 210, an optical coupler 220, a polarizing plate 222, a half wave polarizing plate 224, a RGB combiner 230, a optical fiber array 240 and a light collimator 250.

Referring to FIG. 2, the laser 210 is comprised to generate light, may include a blue (B) laser, a green (G) laser and a red (R) laser to generate white light. That is, the each of the single mode light sources that have wavelength corresponding red, blue and green color is divided into optical fibers having different paths by the respective optical couplers 220, and the lights of respective wavelength, R, G and B may be mixed by the additive color mixture by the RGB combiner 230. According to an embodiment of the present invention, the laser 210 generates coherent and beam shaped light, and the diameter thereof may be more or less than a few millimeters, but not necessarily limited thereto. However, in order for the beam generated by the laser to be entered to the spatial light modulator 290 having size of a few centimeters or more, it may be required to magnify the diameter of the incident light to be hundreds times or more. The laser 210 may be a single mode optical fiber laser. That is, the beam of one path is diverged into several paths using the optical coupler 220, and the diverged bundles of the optical fibers may irradiate light on the spatial light modulator 290 as an optical fiber array. It is available for each end of the diverged optical fiber to have large numerical aperture using the lens-shaped optical fiber which is shaped to have the form of lens. That is, the optical collimator 250 for generating collimated coherent light which the same area with that of the spatial light modulator 290 for system construction may be a lens-shaped optical fiber, through this, the problem of not being suitable for portable devices since the conventional collimator needs a huge complex optical device structure of high price in order to expand beams may be solved. The polarization direction of light sources and the intensity of light may be controlled by installing the polarizing plate 222 and the half wave polarizing plate 224 at each of the single wavelength optical fiber parts between the optical coupler 220 and the combiner 230.

Figure 3:
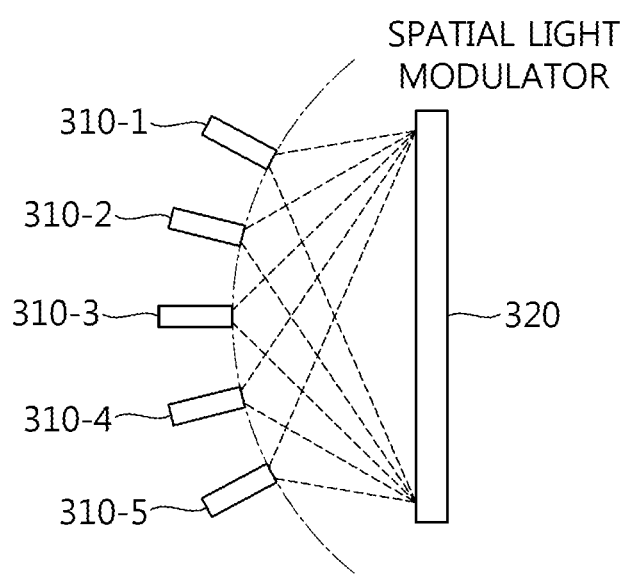
FIG. 3 is a drawing illustrating the light source array arranged in an arc shape in a holographic display apparatus according to an embodiment of the present invention.

FIG. 3 is a drawing illustrating the light source array arranged in an arc shape in a holographic display apparatus according to an embodiment of the present invention.

Referring to FIG. 3, light source array 310-1, 310-2, 310-3, 310-4 and 310-5 may be arranged in an arc shape.

Like this, by arranging the light source array 310-1, 310-2, 310-3, 310-4 and 310-5 in an arc shape, the hologram can be arranged without the observable view without being overlapped. The beams that enter the spatial light modulator 320 through the light source array 310-1, 310-2, 310-3, 310-4 and 310-5 arranged in an arc shape are modulated and diffracted by the CGH which is generated by a hologram generating unit, and the diffracted light waves on each axis may form a viewing window array on the focal plane of the lens by passing through a fattener lens.

Figure 4:
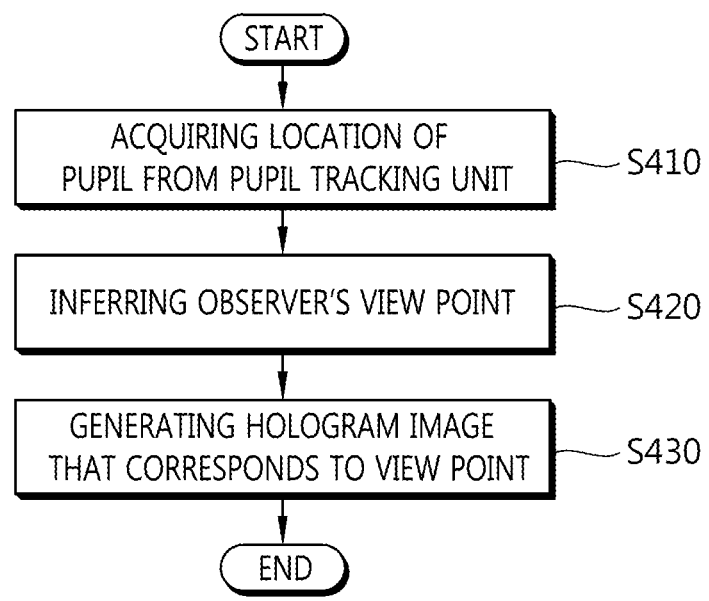
FIG. 4 is a flow chart illustrating the procedure of generating the hologram images according to the location of pupil performed by the hologram generating unit of the holographic display apparatus according to an embodiment of the present invention.

FIG. 4 is a flow chart illustrating the procedure of generating the hologram images according to the location of pupil performed by the hologram generating unit of the holographic display apparatus according to an embodiment of the present invention.

Referring to FIG. 4, the hologram generating unit acquires the pupil location information from the pupil tracking unit (step, S410). Thus, the view point of an observer may be inferred based on the acquired pupil location information (step, S420). Since the holographic display apparatus according to an embodiment of the present invention has the structure of minimizing the viewing angle in order to maximize the size of a screen, the viewing angle of the images becomes extremely narrow and thus the observer may not observe the hologram images properly without performing the view point inference through tracking the pupil of the observer. As described above, although a wide viewing angle may be secured by arraying the viewing window without being overlapped by light array, if the pupil location of the observer, that is, the view point is changed. It can be a problem that the hologram images observed in different view point are also observed as the hologram of the identical view point. Accordingly, the hologram generating unit generates the hologram images that correspond to the inferred view point of the observer (step, S430). The method for generating the hologram images that correspond to the view point of the observer will be described by referring to FIG. 5.

Figure 5:
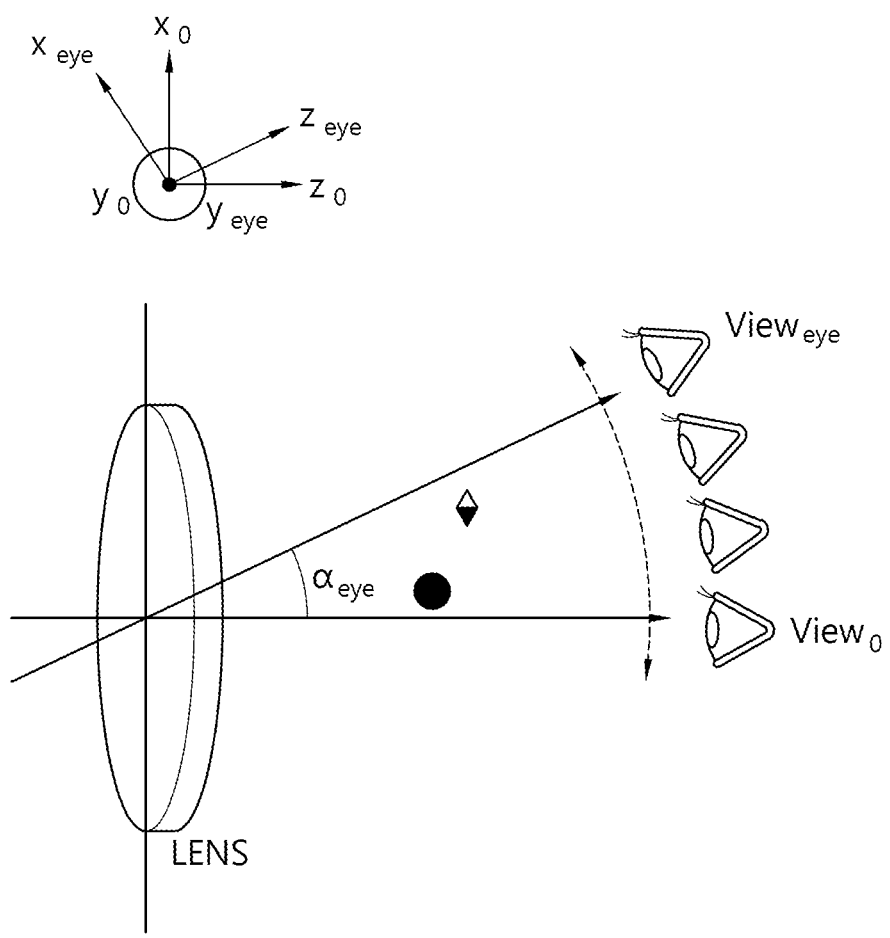
FIG. 5 is a conceptual view for describing the principle of providing parallax images performed by the hologram generating unit of the holographic display apparatus according to an embodiment of the present invention.

FIG. 5 is a conceptual view for describing the principle of providing parallax images performed by the hologram generating unit of the holographic display apparatus according to an embodiment of the present invention.

Referring to FIG. 5, in order to generate the hologram which is to be played by the spatial light modulator, the rotation of the axis of input images is required according to the optical axis of the respective viewing windows generated by the light source array. The reference axis ($x_0$, $y_0$ and $z_0$) which is the center of all axes is the axis identical to the optical axis of lens. Accordingly, the images rotated along the axis with as much as the angle ($\alpha_{eye}$) between the axis ($x_{eye}$, $y_{eye}$ and $z_{eye}$) connecting the location of pupil (View$_{eye}$) tracked by the pupil tracking unit and the center of the lens and the reference axis are set up as images played. In this time, the rotational direction of the axis may be set up in the direction toward the reference axis from the axis of pupil. This can be mathematically expressed as follows.

$$\begin{pmatrix} x_{eye} \\ y_{eye} \\ z_{eye} \end{pmatrix} = \begin{pmatrix} \sin\alpha_{eye} & 0 & \cos\alpha_{eye} \\ 0 & 1 & 0 \\ \cos\alpha_{eye} & 0 & -\sin\alpha_{eye} \end{pmatrix} \begin{pmatrix} x_0 \\ y_0 \\ z_0 \end{pmatrix}$$ [Equation 1]

Herein, $x_{eye}$, $y_{eye}$ and $z_{eye}$ are coordinates of the axes connecting the location of pupil and the center of lens, $x_0$, $y_0$ and $z_0$ mean the reference axis which is the center of all axes, and $\alpha_{eye}$ is an angle between $x_{eye}$, $y_{eye}$ and $z_{eye}$ and $x_0$, $y_0$ and $z_0$.

Through the calculation using Equation 1, the hologram images according to the view point that corresponds to the location of the pupil of an observer may be reproduced.

Figure 6:
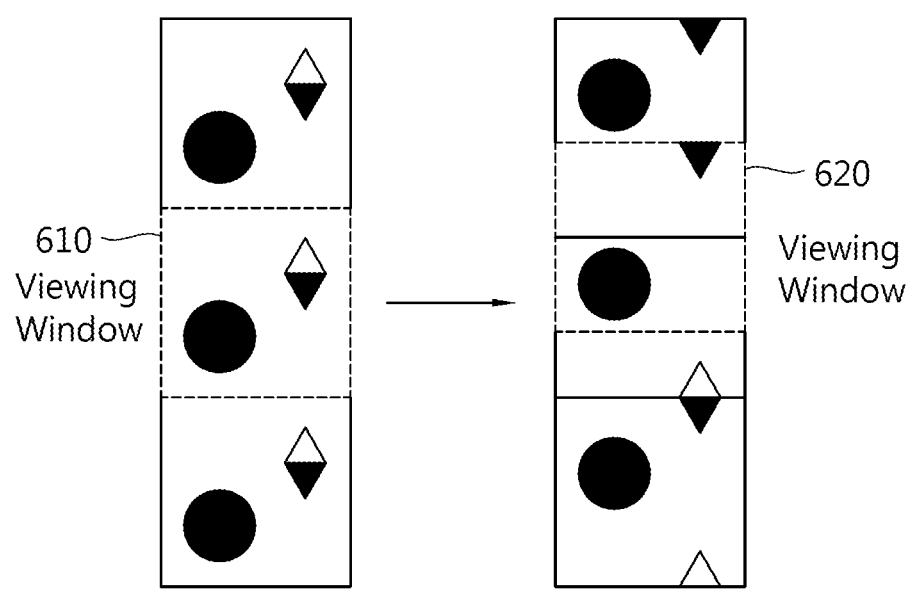
FIG. 6 is a conceptual view for describing the off-axis hologram encoding performed by the holographic display apparatus according to an embodiment of the present invention.

FIG. 6 is a conceptual view for describing the off-axis hologram encoding performed by the holographic display apparatus according to an embodiment of the present invention.

Referring to FIG. 6, the hologram generating unit of the holographic display apparatus according to an embodiment of the present invention executes the off-axis hologram encoding and moves a viewing window 610 to a next viewing window 620. As shown in the left part of FIG. 6, in order to supplement the gap that exists between viewing windows, the viewing window may be shifted. That is, as shown in right part of FIG. 6, the gap may be supplemented by changing the location of the viewing window within the corresponding region. This may be performed using the following equation.

$$\text{Hologram}_{off\text{-}axis}(x,y) = \text{Hologram}_{on\text{-}axis}(x,y) * \exp(j \cdot 2\pi \cdot \sin\theta \cdot x/\lambda)$$ [Equation 2]

$\lambda$: Wavelength
$\theta$: Off-axis angle

Herein, Hologram$_{off\text{-}axis}$ (x, y) represents x and y coordinates of being off-axis, Hologram$_{on\text{-}axis}$ (x, y) represents x and y coordinates before being off-axis, $\lambda$ represents wavelength and $\theta$ represents off-axis angle. The hologram generating unit supplements the gap by changing the location of viewing window using the equation above.

Figure 7:
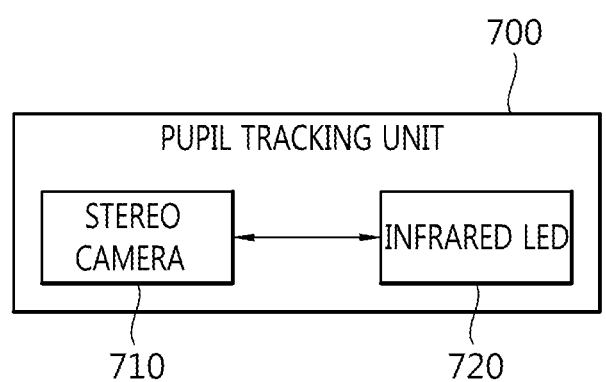
FIG. 7 is a detailed block diagram illustrating the construction of the pupil tracking unit of the holographic display apparatus according to an embodiment of the present invention.

FIG. 7 is a detailed block diagram illustrating the construction of the pupil tracking unit of the holographic display apparatus according to an embodiment of the present invention. As shown in FIG. 7, the pupil tracking unit 700 according to an embodiment of the present invention may include a stereo camera 710 and an infrared LED 720.

Referring to FIG. 7, the stereo camera 710 acquires the location of observer's pupil. The location of pupil acquired is utilized for inferring the view point of the observer through the hologram generating unit. The stereo camera 710 may acquire the 3-dimensional information which is in relation to the location of observer's pupil. Since the stereo camera 710 should track the location of pupil at the side of the display played, it is preferable to be disposed in front of the display.

The infrared LED 720 may be operated when the light is dark around, and then support tracking of observer's pupil performed by the stereo camera 710. The infrared LED 720 may also be disposed in front of the display together with the stereo camera 710.

So far, the present invention has been described with reference to the drawings and the embodiments, which does not mean the scope of the present invention is not limited thereto, and it should be understood by those skilled in the art, however, that the present invention can be modified or changed in various ways without departing from the technical principles and scope.

What is claimed is:
1. A holographic display apparatus, comprising:
    a light irradiating unit configured to irradiate light using an optical fiber array backlight;
    a spatial light modulator (SLM) configured to perform modulating the irradiated light;
    a lens configured to irradiate hologram images based on the modulated light;

a pupil tracking unit configured to acquire a location of an observer's pupil by pupil tracking; and a hologram generating unit configured to generate parallax hologram images that correspond to the location of the pupil, wherein the light irradiating unit comprises a viewing window array provided by arranging a light source array in an arc shape with respect to horizontal and vertical directions.

2. The holographic display apparatus of claim 1, wherein the hologram generating unit changes a location of a viewing window included in the viewing window array by performing off-axis hologram encoding when generating a hologram in order to supplement a spatial gap between viewing windows included in the viewing window array.

3. The holographic display apparatus of claim 1, wherein the light irradiating unit comprises an optical fiber laser and an optical fiber.

4. The holographic display apparatus of claim 3, wherein the light irradiating unit comprises:

an optical fiber coupler configured to diverge the optical fiber laser beam into paths; and a RGB combiner configured to generate white light using the diverged optical fiber laser beam.

5. The holographic display apparatus of claim 4, wherein the light irradiating unit comprises:

a half wave polarizing plate and a polarizing plate installed between respective optical fibers that are diverged into several parts in order to control a polarization direction of an incident beam and a power of light; and a light collimator installed at a terminal of the optical fiber in order to irradiate plane waves to the spatial light modulator.

6. The holographic display apparatus of claim 1, further comprising a noise mask configured to filter diffracted high-order terms and twin images.

7. The holographic display apparatus of claim 6, wherein the lens is a field flattener lens, and wherein a viewing window included in the viewing window array is formed at a focal distance by focusing the modulated light into a focal point of the lens.

8. The holographic display apparatus of claim 1, wherein the pupil tracking unit comprises a stereo camera and an infrared LED.

9. A holographic display method, comprising:

irradiating light using an optical fiber array backlight;

modulating the irradiated light performed by a spatial light modulator (SLM);

irradiating hologram images by passing the modulated light through a lens;

tracking a pupil for acquiring a location of an observer's pupil by pupil tracking; and generating parallax hologram images that correspond to the location of the pupil, wherein irradiating the light comprises diverging optical fiber laser beam into paths and generating white light through an RGB combiner.

10. The holographic display method of claim 9, wherein generating the hologram images comprises changing a location of a viewing window by performing off-axis hologram encoding when generating a hologram in order to supplement spatial gap between viewing windows.

11. The holographic display method of claim 10, wherein irradiating the light comprises:

controlling a polarization direction of incident beam and power of light by installing a half wave polarizing plate and a polarizing plate between respective optical fibers that are diverged into several parts; and irradiating a plane wave to the spatial light modulator through a light collimator installed at a terminal of the optical fiber.

12. The holographic display method of claim 9, further comprising filtering diffracted high-order terms and twin images by a noise mask.

13. The holographic display method of claim 9, wherein the lens is a field flattener lens, and wherein irradiating the hologram comprises forming a viewing window at a focal distance by focusing the modulated light into a focal point of the lens.

14. The holographic display method of claim 9, wherein tracking the pupil comprises acquiring the location of the observer's pupil using a stereo camera and an infrared LED.

15. A holographic display method, comprising:

irradiating light using an optical fiber array backlight;

modulating the irradiated light performed by a spatial light modulator (SLM);

irradiating holograms images by passing the modulated light through a lens;

tracking a pupil for acquiring a location of an observer's pupil by pupil tracking; and generating parallax hologram images that correspond to the location of the pupil, wherein irradiating the light comprises forming a viewing window array provided by arranging a light source array in an arc shape with respect to horizontal and vertical directions.

* * * * *